(12) United States Patent
    Siever

(10) Patent No.: US 11,322,042 B2
(45) Date of Patent: May 3, 2022

(54) TECHNOLOGIES FOR AUDIO-VISUAL ENTRAINMENT WITH BREATHING CUES FOR MANAGING HEART RATE VARIABILITY

(71) Applicant: Mind Alive Inc., Edmonton (CA)

(72) Inventor: David Siever, Edmonton (CA)

(73) Assignee: Mind Alive Inc., Edmonton (CA)

( * ) Notice: Subject to any disclaimer, the term of this patent is extended or adjusted under 35 U.S.C. 154(b) by 0 days.

(21) Appl. No.: 17/117,475

(22) Filed: Dec. 10, 2020

(65) Prior Publication Data

US 2021/0183262 A1 Jun. 17, 2021

Related U.S. Application Data

(60) Provisional application No. 62/946,716, filed on Dec. 11, 2019.

(51) Int. Cl.
    *G09B 19/00* (2006.01)
    *A61B 5/024* (2006.01)
    *G09B 5/06* (2006.01)
    *G06F 3/16* (2006.01)

(52) U.S. Cl.
    CPC .......... *G09B 19/00* (2013.01); *A61B 5/02405* (2013.01); *G09B 5/06* (2013.01); *G06F 3/165* (2013.01)

(58) Field of Classification Search
    CPC .......... G06F 3/16; G06F 3/165; A61M 21/00; G09B 19/00; G09B 5/06; A61B 5/02; A61B 5/02405
    See application file for complete search history.

(56) References Cited

U.S. PATENT DOCUMENTS

| 4,315,502 | A | 2/1982 | Gorges |
| 5,599,274 | A | 2/1997 | Widjaja et al. |
| 5,709,645 | A | 1/1998 | Siever |
| 6,544,165 | B1 * | 4/2003 | McNew ............ A61M 21/0094 600/27 |
| 10,737,054 | B1 * | 8/2020 | Lynn ..................... A61M 21/02 |
| 2005/0149144 | A1 | 7/2005 | Siever |

FOREIGN PATENT DOCUMENTS

| DE | 3823402 | 1/1990 |
| RU | 2336020 | 10/2008 |
| WO | WO2019/074637 | 4/2019 |

* cited by examiner

*Primary Examiner* — Timothy A Musselman
(74) *Attorney, Agent, or Firm* — Dentons US LLP

(57) ABSTRACT

This discloses enables various technologies for audio-visual entrainment with breathing cues for managing heart rate variability.

20 Claims, 9 Drawing Sheets

TECHNOLOGIES FOR AUDIO-VISUAL ENTRAINMENT WITH BREATHING CUES FOR MANAGING HEART RATE VARIABILITY

CROSS-REFERENCE TO RELATED PATENT APPLICATION

This patent application claims a benefit of U.S. Provisional Patent Application 62/946,716 filed 11 Dec. 2019, which is herein incorporated by reference for all purposes as if copied and pasted herein.

TECHNICAL FIELD

This patent application relates to medical technologies for stimulating the mammalian central nervous system using audio-visual entrainment together with breathing cues for managing heart rate and heart rate variability.

BACKGROUND

Heart rate variability (HRV) is the variation in the time between each heartbeat. HRV is related but different than heart rate (HR), which is measured by the number of times a person's heart beats per minute. Unlike heart rate, which can be calculated by counting your pulse, heart rate variability is typically measured using an electrocardiogram (ECG or EKG) or similar device that records the electrical activity of a person's heart.

HRV is a good measure of the efficiency and performance of a person's cardiovascular system. A high HRV is a good indicator of general health with less risk of disease. A lower HRV is associated with heart attacks, strokes, and diabetes (for example).

Heart rate variability may also be a marker of how well a person's body can handle stress. With a higher HRV, a person can typically perform well under duress. A low HRV, and it will be difficult to bounce back after a stressful situation.

The failings with traditional technologies for managing HRV is that the more anxious the person is, the worse that person typically performs at the task. Highly anxious persons are so agitated and overwhelmed with racy-headed thoughts, that the persons often cannot or unable to follow the most basic of instructions, such as cuing when to breathe in and breathe out. So, traditional HR/HRV training fails in the people who are in most need of it.

Consequently, there is a desire for a technology to enable stimulation of the mammalian central nervous system, such as neuron and the glia, using audio-visual entrainment together with breathing cues for managing HRV to at least one of prevent, diagnose, monitor, ameliorate, or treat a medical condition, a disease, or a disorder of a patient, such as a mammal, such as an animal, such as a human, whether male or female, whether infant, child, adult, or elderly, or others. However, such technology is not known to exist. Therefore, this disclosure enables such technology.

SUMMARY

Certain exemplary embodiments can provide a method comprising: causing a headwear unit to be worn by a user having a right eye and a left eye, wherein the right eye has a first right visual field and a first left visual field, wherein the left eye has a second right visual field and a second left visual field, wherein the headwear unit hosts a processor, a first light source configured for stimulating the first right visual field of the right eye and the first left visual field of the right eye when requested by the processor while the headwear unit is worn by the user, and a second light source configured for stimulating the second right visual field of the left eye and the second left visual field of the left eye when requested by the processor while the headwear unit is worn by the user; causing the processor to read a first set of parameters, a second set of parameters, and a third set of parameters, wherein the first set of parameters includes a first-left-color (AL) identifier, a first-right-color (AR) identifier, a first light frequency range, and a first time duration, wherein the second set of parameters includes a second-left-color (BL) identifier, a second-right-color (BR) identifier, a second light frequency range, and a second time duration, and wherein the third set of parameters includes a third-left-color (CL) identifier, a third-right-color (CR) identifier, a third light frequency range, and a third time duration; causing the processor to request the first light source and the second light source (a) to flash a first-left-color, within the first light frequency range, to the first left visual field and the second left visual field for the first time duration based on the first-left-color (AL) identifier and (b) to flash a first-right-color, within the first light frequency range, to the first right visual field and the second right visual field for the first time duration based on the first-right-color (AR) identifier; causing the processor to request the first light source and the second light source (a) to flash a second-left-color, within the second light frequency range, in the first left visual field and the second left visual field for the second time duration based on the second-left-color (BL) identifier and (b) to flash a second-right-color, within the second light frequency range, in the first right visual field and the second right visual field for the second time duration based on the second-right-color (BR) identifier such that the user is visually instructed to start an inspiration and hold of breath phase; causing the processor to request the first light source and the second light source (a) to change from flashing the second-left-color to a third-left-color, within the third light frequency range, in the first left visual field and the second left visual field based on the third-left-color (CL) identifier and (b) to change the second-right-color to a third-right-color, within the third light frequency range, in the first right visual field and the second right visual field based on the third-right-color (CR) identifier such that the user is visually instructed to start an expiration of breath phase to the user after the inspiration and hold of breath phase; and causing the processor to request a heart rate monitor to monitor at least one of a heart rate of the user or a heart rate variability of the user throughout at least one of the inspiration and hold breath phase or the expiration of breath phase until the third time duration expires.

Certain exemplary embodiments can provide a memory storing a set of instructions executable by a processor of a headwear unit when the headwear unit is worn by a user having a right eye and a left eye, wherein the right eye has a first right visual field and a first left visual field, wherein the left eye has a second right visual field and a second left visual field, wherein the headwear unit hosts a processor, a first light source configured for stimulating the first right visual field of the right eye and the first left visual field of the right eye when requested by the processor while the headwear unit is worn by the user, and a second light source configured for stimulating the second right visual field of the left eye and the second left visual field of the left eye when requested by the processor while the headwear unit is worn by the user, wherein the set of instructions causes the processor to: read a first set of parameters, a second set of parameters, and a third set of parameters, wherein the first set of parameters includes a first-left-color (AL) identifier, a first-right-color (AR) identifier, a first light frequency range, and a first time duration, wherein the second set of parameters includes a second-left-color (BL) identifier, a second-right-color (BR) identifier, a second light frequency range, and a second time duration, and wherein the third set of parameters includes a third-left-color (CL) identifier, a third-right-color (CR) identifier, a third light frequency range, and a third time duration; request the first light source and the second light source (a) to flash a first-left-color, within the first light frequency range, to the first left visual field and the second left visual field for the first time duration based on the first-left-color (AL) identifier and (b) to flash a first-right-color, within the first light frequency range, to the first right visual field and the second right visual field for the first time duration based on the first-right-color (AR) identifier; request the first light source and the second light source (a) to flash a second-left-color, within the second light frequency range, in the first left visual field and the second left visual field for the second time duration based on the second-left-color (BL) identifier and (b) to flash a second-right-color, within the second light frequency range, in the first right visual field and the second right visual field for the second time duration based on the second-right-color (BR) identifier such that the user is visually instructed to start an inspiration and hold of breath phase; request the first light source and the second light source (a) to change from flashing the second-left-color to a third-left-color, within the third light frequency range, in the first left visual field and the second left visual field based on the third-left-color (CL) identifier and (b) to change the second-right-color to a third-right-color, within the third light frequency range, in the first right visual field and the second right visual field based on the third-right-color (CR) identifier such that the user is visually instructed to start an expiration of breath phase to the user after the inspiration and hold of breath phase; and request a heart rate monitor to monitor at least one of a heart rate of the user or a heart rate variability of the user throughout at least one of the inspiration and hold breath phase or the expiration of breath phase until the third time duration expires.

Certain exemplary embodiments can provide a device including: a headwear unit configured to be worn by a user having a right eye and a left eye, wherein the right eye has a first right visual field and a first left visual field, wherein the left eye has a second right visual field and a second left visual field, wherein the headwear unit hosts a processor, a first light source configured for stimulating the first right visual field of the right eye and the first left visual field of the right eye when requested by the processor while the headwear unit is worn by the user, and a second light source configured for stimulating the second right visual field of the left eye and the second left visual field of the left eye when requested by the processor while the headwear unit is worn by the user, wherein the processor is programmed to: read a first set of parameters, a second set of parameters, and a third set of parameters, wherein the first set of parameters includes a first-left-color (AL) identifier, a first-right-color (AR) identifier, a first light frequency range, and a first time duration, wherein the second set of parameters includes a second-left-color (BL) identifier, a second-right-color (BR) identifier, a second light frequency range, and a second time duration, and wherein the third set of parameters includes a third-left-color (CL) identifier, a third-right-color (CR) identifier, a third light frequency range, and a third time duration; request the first light source and the second light source (a) to flash a first-left-color, within the first light frequency range, to the first left visual field and the second left visual field for the first time duration based on the first-left-color (AL) identifier and (b) to flash a first-right-color, within the first light frequency range, to the first right visual field and the second right visual field for the first time duration based on the first-right-color (AR) identifier; request the first light source and the second light source (a) to flash a second-left-color, within the second light frequency range, in the first left visual field and the second left visual field for the second time duration based on the second-left-color (BL) identifier and (b) to flash a second-right-color, within the second light frequency range, in the first right visual field and the second right visual field for the second time duration based on the second-right-color (BR) identifier such that the user is visually instructed to start an inspiration and hold of breath phase; request the first light source and the second light source (a) to change from flashing the second-left-color to a third-left-color, within the third light frequency range, in the first left visual field and the second left visual field based on the third-left-color (CL) identifier and (b) to change the second-right-color to a third-right-color, within the third light frequency range, in the first right visual field and the second right visual field based on the third-right-color (CR) identifier such that the user is visually instructed to start an expiration of breath phase to the user after the inspiration and hold of breath phase; and request a heart rate monitor to monitor at least one of a heart rate of the user or a heart rate variability of the user throughout at least one of the inspiration and hold breath phase or the expiration of breath phase until the third time duration expires.

DETAILED DESCRIPTION

Figure 1:
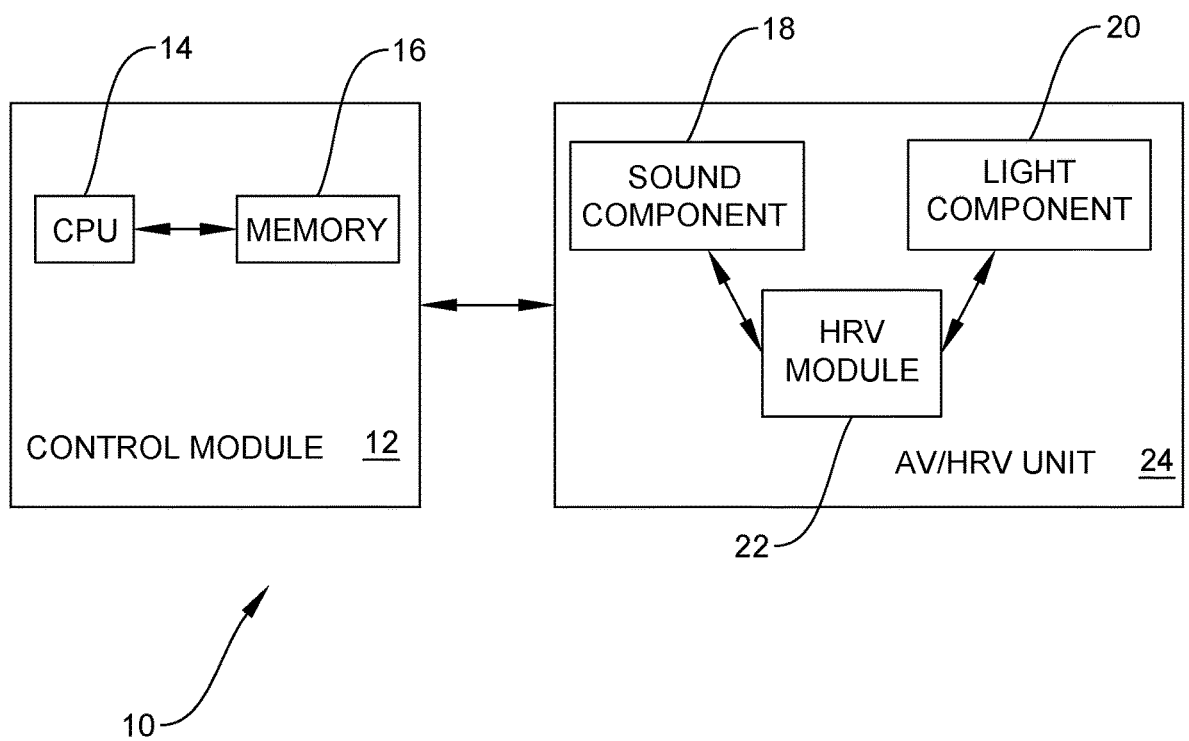
FIG. 1 illustrates an embodiment of an audio-visual entrainment system used to implement various methods according to this disclosure.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Various terminology used herein is for describing example embodiments and is not intended to be necessarily limiting of this disclosure. As used herein, various singular forms "a," "an" and "the" are intended to include various plural forms (e.g., 2, 3, 4, 5, 6, 7, 8, 9, 10, tens, hundreds, thousands) as well, unless a context clearly indicates otherwise.

Various terms, such as "comprises," "includes" and/or "comprising," "including", when used in this specification, specify a presence of stated features, integers, steps, operations, elements, and/or components, but do not preclude the presence and/or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

As used herein, a term "about" and/or "substantially" refers to a +/−10% variation from a nominal value/term. Such variation is always included in any given value/term provided herein, whether or not such variation is specifically referred thereto.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized and/or overly formal sense unless expressly so defined herein.

Generally, the human brain tends to follow rhythm. The electrical activity (EEG) of the human brain is rhythmic and seen as brain waves. For example, when a person listens to music with a fast beat, then that person's brain waves tend to speed up and when a person listens to music with a slow beat, then that person's brain waves tend to slow down. Sometimes, flashing lights can affect brain waves. Flashing a light steadily into the eye will stimulate the brain and cause the brain waves to entrain to the same frequency as the flashing light (i.e., the amplitude of the brain waves, at the same frequency as the flashing light, will increase). Flashing the light faster will increase the amplitude of higher frequency or faster brain waves, whereas flashing the light slower will increase amplitude of lower frequency or slower brain waves and thus affect the arousal of the mind itself. This frequency following effect of brain waves in response to rhythmic stimulation is called brain wave entrainment.

Audio-visual entrainment (AVE) refers to the use of flashing lights and rhythmic tones to purposefully entrain brain waves toward some desired rhythm or frequency, whether statically set or dynamically changing. By stimulating the brain with flashing lights using purpose made glasses (or other forms of headwear) and pulsing tones through head/earphones (or other forms of headwear) it is possible to shift the frequency of the dominant brain waves either higher or lower and thereby change brain function.

Human brains produce four basic brainwave states: beta, alpha, theta and delta. A healthy brain will produce the appropriate brainwaves for a given situation. For example, when sleeping the brain normally shows elevated very low frequency delta activity and reduced amounts of higher frequency theta, alpha and beta waves. By contrast, when awake, the normal brain shows predominantly alpha and beta activity with less theta and very little delta activity. During concentration, beta activity becomes the dominant brain wave rhythm.

Due to stress, neurotransmitter imbalances, genetic factors, brain injury, or other trauma, people may produce too much or too little of certain brain waves for certain activities. For example, people who have trouble falling asleep and/or experience frequent waking during the night do not produce enough very low frequency delta brain waves at bedtime and, when they do manage to fall asleep, will experience frequent bursts of higher frequency alpha activity that will bring them into a wake state. Another problem is seen in people with Attention-Deficit Disorder (ADD), cognitive decline in seniors and dementia such as Alzheimer's Disease that produce too much slow wave theta activity when they try to do mental tasks (i.e., math, reading, etc.).

Heart rate variability (HRV) reflects overall mental and physical health. For instance, during periods of calm, relaxation and meditation, heart rate variability is high. However, during periods of stress, anxiety and trauma, post-traumatic stress disorder, adrenal insufficiency and adrenal fatigue, heart rate variability is diminished greatly. There is a correlation between restricted HRV and the likelihood of death.

Managing HRV is a biofeedback technique that employs the user of a breath pacer to cue a user as to when to breathe in and out. In the process of breathing to a timed breath pacer, it is expected that the heart rhythm (i.e., frequency in beats/minute) will follow in synchronization with the respiration. When the heart rhythm properly follows respiration, the heart rate swings upwards in frequency during inspiration (i.e., a sympathetic response) and slows down (i.e., a parasympathetic vagal response) during expiration. HRV is a biofeedback mechanism of quickly and scientifically achieving meditative breathing or prana.

Establishing a smooth and even heart rhythm cycle calms the autonomic nervous system. The person becomes deeply relaxed with reduced muscle activation, overall heart rate, calm mind, etc. However, the more anxious or agitated a person is or if the person is experiencing acute trauma or post-traumatic stress disorder (PTSD), the ability to follow a regimented breath pacer becomes increasingly difficult to follow and can even increase agitation and anxiety in the effort of trying to breathe and relax. In other words, the very people who need HRV training the most, are also the ones most likely to fail the training.

The methods described in the present application use AVE as an assist for deeply relaxed and effective management of HRV by using color (or other illumination characteristics) changes in the lights that stimulate the visual fields of the eyes and/or tone (or other sound characteristics) changes in the sound signals sent to the ears while simultaneously entraining. The inventor has found that using AVE, which elicits deep relaxation, together with using color (or other illumination characteristics) changes, light intensity and auditory tonal (or other sound characteristics) changes synergistically prompts the user to breath in a deeply calm manner without anxiety as is often seen from the regimented metronome-type of push as with breath pacers. In addition to changing the entraining colors (or other illumination characteristics) and/or tones (or other sound characteristics), the intensity of the lights (or other illumination characteristics) and the loudness of the tones (or other sound characteristics) increases during the inspiration phase of the breath cycle and decreases during the expiration portion of the breath cycle. This effect feels natural to the user and compels the user to breathe in and out in a natural and gentle way.

For example, the described technologies (e.g., methods, devices, etc.) can be configured to prevent, diagnose, monitor, ameliorate, or treat neurological, neuropsychological, or neuropsychiatric activity, such as a modulation of neuronal function or processing to affect a functional outcome. The modulation of neuronal function can be useful regarding diagnosing, monitoring, preventing, treating, or ameliorating neurological, psychiatric, psychological, conscious state, behavioral, mood, or thought activity. For example, this activity can manifests itself in a form of a disorder, such as attention or cognitive disorders (e.g., Autistic Spectrum Disorders), mood disorder (e.g., major depressive disorder, bipolar disorder, dysthymic disorder), anxiety disorder (e.g., panic disorder, post-traumatic stress disorder, obsessive-compulsive disorder, phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, enhancing or diminishing any neurological or psychiatric function not just an abnormality or disorder or others, as understood to skilled artisans and which are only omitted here for brevity.

Neurological activity that may be modulated can include normal functions, such as alertness, conscious state, drive, fear, anger, anxiety, repetitive behavior, impulses, urges, obsessions, euphoria, sadness, and the fight or flight response, as well as instability, vertigo, dizziness, fatigue, photophobia, concentration dysfunction, memory disorders, headache, dizziness, irritability, fatigue, visual disturbances, sensitivity to noise (misophonia, hyperacusis, phonophobia), judgment problems, depression, symptoms of traumatic brain injury (whether physical, emotional, social, or chemical), autonomic functions, which includes sympathetic or parasympathetic functions (e.g., control of heart rate), somatic functions, or enteric functions.

FIG. 1 illustrates an embodiment of an AVE/HRV system 10 used to implement various methods of various embodiments according to this disclosure. The system 10 includes a control module 12 and an AV/HRV unit 24, in signal communication with each other.

The control module 12 (e.g. a housing) includes a processor 14 (e.g., a CPU) and a memory 16 (e.g., a flash memory), where the processor 14 controls at least some, many, most, or all operations of an audio-visual (AV)/HRV unit 24 based on various instructions stored in the memory 16.

Figure 2:
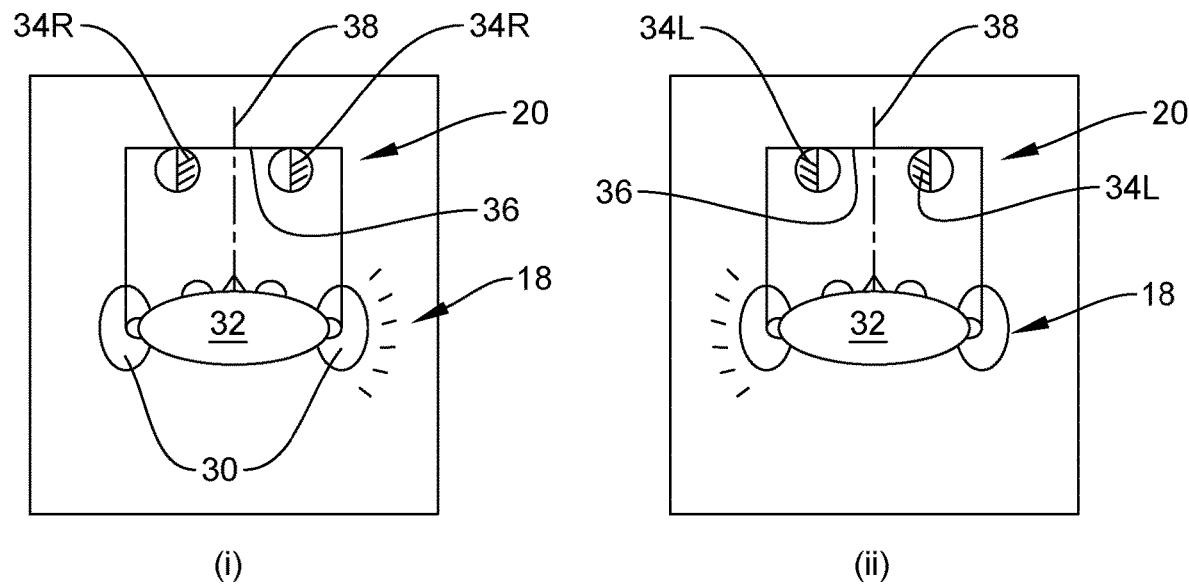
FIG. 2 illustrates an embodiment of various audio and visual stimulation components shown in FIG. 1 according to this disclosure.
Figure 3:
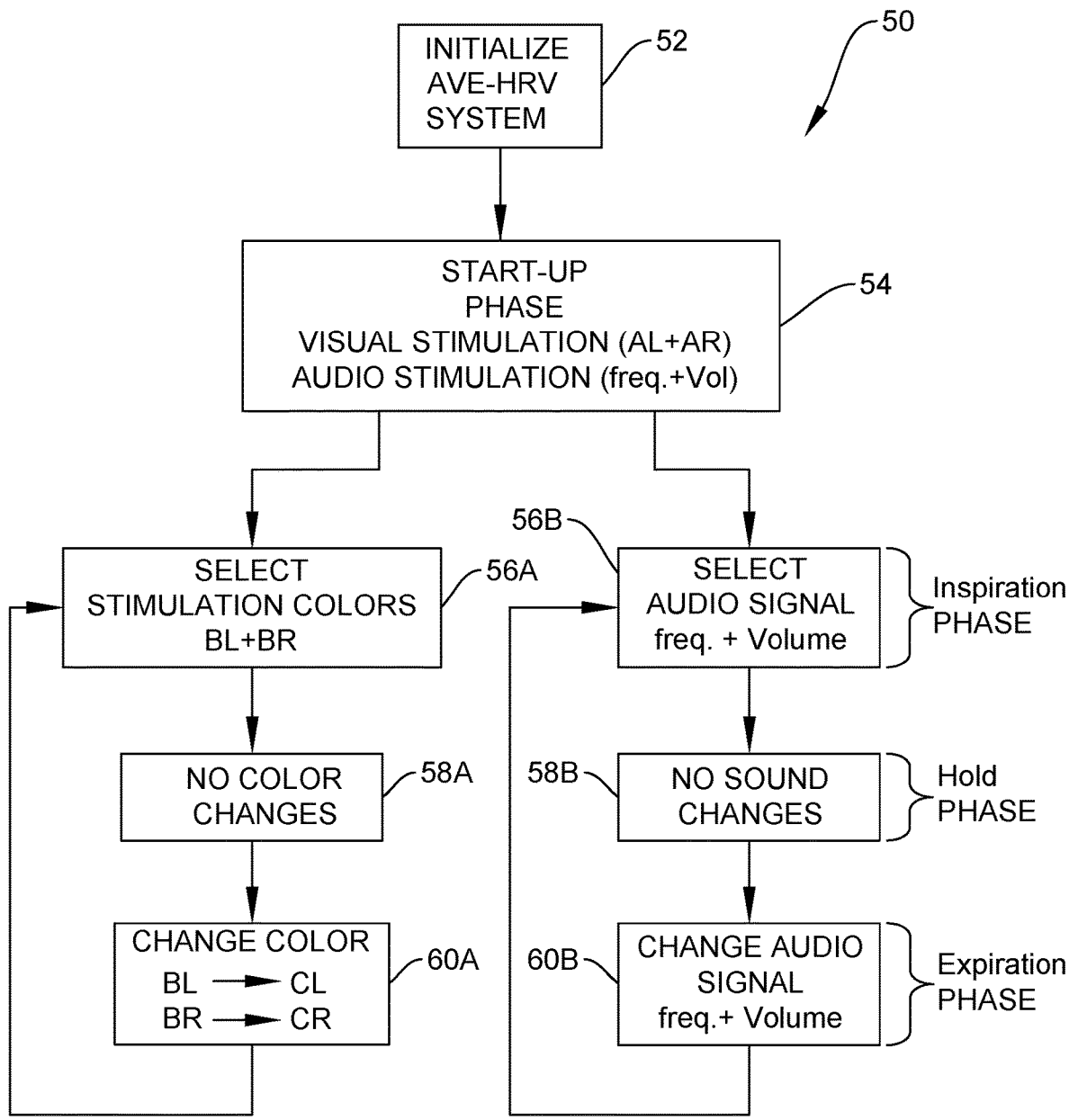
FIG. 3 illustrates an embodiment of a flow chart illustrating a method with breathing cues for managing heart rate variability (HRV) using the system of FIG. 1 according to this disclosure.

The AV/HRV unit 24 includes a sound producing and stimulating component 18 (e.g., a speaker), a light producing and stimulating component 20 (e.g., a light source, a lamp, a bulb) and an HRV module 22 (e.g., a processing circuit housed within a housing) that communicably interacts or interfaces with the component 18 and the component 20 in order to establish, generate, or output various appropriate visual and auditory cues (e.g., a visual content, an audio content) together with monitoring heart rate characteristics (including HRV), as will be explained with reference to FIGS. 2 and 3. The HRV module 22 includes standard HRV sensors and associated processing software available from, for example, Heart Math (EmWave PC); Thought Technologies (CardioPro); and Nexus (Biotrace). For example, the HRV module 22 can include a sensor that measures HRV through pulse detection a multiwave sensor array that conveniently and comfortably slips over a user's finger.

The autonomic nervous system is closely tied to heart rate and its smooth transition between in and out breaths. The autonomic nervous system has two components (sympathetic), which is tied to increased arousal, including fight-or-flight, adrenal activation, adrenalin and cortisol. The parasympathetic system is tied to the vagal response, calming, peaceful feelings, bodily regeneration & repair.

During inhalation, the heart rate speeds up (sympathetic/adrenal/cortisol response) and during exhalation, the heart rate slows down (parasympathetic/vagal response). If a person breathes too fast or too slow, then the person develops anxiety, and that anxiety shows up as both slow and fast frequency activity (autonomic arousal).

The presently described technologies provide AVE assisted breathing to help manage a user's HRV. Initially, the breath rate is set to a level that is generally appropriate for the size of the person and then the breath rate or the level is slowed down by about 0.5 Hz-about 1 Hz. The HRV module 22 can be configured to slowly increase or decrease breathing frequency or the breath rate over a pre-set range. For a petite person (e.g., an adult male between 18 and 65 years of age and having a 5'10 height and a weight of 180 pounds), the pre-set range can be about 6 Hz to about 8 Hz. The breath cycle (which is indicated by the colors changing in an eye set or the light component 20: described in more detail herein) can slowly change (e.g., gradually within 60 minutes) and using the HRV module 22, the user (or third party reviewer) can monitor (e.g., visually) for the maximum peak-to-peak swing in breathing frequency and lowest activity in the low (sympathetic) and lowest activity in the high (parasympathetic) frequency.

Referring to FIG. 2, the sound producing and stimulating component 18 includes headphones/earphones 30 to direct sound signals to the ears (right and left) of a person 32. The basic properties of the sound, which can be altered by the sound component 18, include pitch, loudness, and tone. The frequency of a sound wave is what the ear understands as pitch. A higher frequency sounds has a higher pitch, and a lower frequency sound has a lower pitch. The amplitude of a sound wave determines its loudness or volume. A larger amplitude means a louder sound and a smaller amplitude means a softer sound. The loudness of a sound is also determined by the sensitivity of the ear. The human ear is more sensitive to some frequencies than to others. The volume a human receives, and processes thus depends on both amplitude of a sound wave and whether its frequency lies in a region where the ear is sensitive. Tone can be defined as sound that is recognized by its regularity of vibration. A simple tone has only one frequency, although intensity may vary. A complex tone consists of two or more simple tones.

The light producing and stimulating component 20 includes a plurality of light sources 34L/34R (e.g., bulbs, lamps, LEDs) arranged on a pair of glasses/eye pieces 36 that direct light toward the eyes (right and left) of the person 32 (e.g., male, female). For example, the pair of glasses or an headset or headwear unit may have a frame with an arm or a pair of arms, any of which may be independently or dependently pivoting with respect to the frame for folding purposes, where the light sources 34L/34R may be mounted on the frame. The light sources 34L/34R change color and intensity to provide the breathing cues for HRV management, as discussed herein. The unit 24 may optionally host a blocker 38 that may be placed or extend between the sets of light sources in each light-producing assembly 34L/34R, to prevent or effectively minimize light sources from illuminating more than their associated visual field. Note that the unit 24 can be embodied, whether additionally or alternatively, as an optical head-mounted display, a hat, a helmet, a head-worn frame, an earpiece, or others.

The light sources 34L/34R produce light and the headphones 30 produce sound in response to light and audio signals, respectively, provided by one or both of the control module 12 and the HRV module 22, whether physically hosted via the unit 24 or not physically hosted via the unit 24. For example, the pair of glasses or an headset or headwear unit may have a frame with an arm or a pair of arms, any of which may be independently or dependently pivoting with respect to the frame for folding purposes, where the sound producing and stimulating component 18 may be mounted on the arm or both arms.

U.S. Pat. No. 5,709,645, incorporated herein by reference for all purposes, is an example AVE system 10 that can deliver visual signals to the left and right visual fields of each eye and sound signals to the ears. In general, the photic device includes an eye mask with independent left and right eye pieces and means of fitting the eye mask over the subject's eyes. Each eyepiece contains a dedicated light-producing assembly having two independent sets of light sources, one for each of the left and right visual fields of each eye. Each of the light sources is independently operable to pulse light into the corresponding visual field of each eye, thereby stimulating that visual field. An optional blocker may be placed between the sets of light sources in each light-producing assembly, to prevent light sources from illuminating more than their associated visual field.

Referring to FIG. 3, an embodiment of a method 50 for audio-visual entrainment with breathing cues for training heart rate variability (HRV) is illustrated according to this disclosure. The AVE/HRV system 10 is initialized at step 52 to boot up or power up (whether mains or battery powered) and initialize to a start-up operation condition the control module 12 and all components of the AV/HRV unit 24. In particular, the control module 12 is configured to obtain (e.g., retrieve, read, generate) a first set of parameters, a second set of parameters, and a third set of parameters from the control module 12 (e.g., the memory 16), wherein the first set of parameters includes a first-left-color (AL) identifier, a first-right-color (AR) identifier, a first light frequency range, and a first time duration, wherein the second set of parameters includes a second-left-color (BL) identifier, a second-right-color (BR) identifier, a second light frequency range, and a second time duration, and wherein the third set of parameters includes a third-left-color (CL) identifier, a third-right-color (CR) identifier, a third light frequency range and a third time duration.

Optionally, sound stimulation parameters (e.g., a tone, a pitch, a volume, a duration) for operating the sound component 18 can also be obtained at step 52. Note that each member of the first set of parameters can be identical or non-identical in value or format to each respective member of the second set of parameters or the third set of parameters. Likewise, each member of the second set of parameters can be identical or non-identical in value or format to each respective member of the first set of parameters or the third set of parameters. Similarly, each member of the third set of parameters can be identical or non-identical in value or format to each respective member of the first set of parameters or the second set of parameters.

Example initial default settings at the start-up phase 52 are about four (4) seconds for the in-breath (inspiration phase), about 0.5 seconds for breath-hold and about six (6) seconds for the out-breath (expiration phase). A sample default setting for the visual frequency can be set to about 7.8 Hz. This frequency of 7.8 Hz is on the alpha-theta border or "thalpha" and can also referred as the Schumann Resonance frequency. However, this frequency is user adjustable from (about 0.1 Hz (sub-delta) to about 50 Hz (gamma)) using the control module 12 (e.g., via a user input device, a touchscreen, a keyboard, a button, a switch, a dial, a knob, a slider, a cursor device, a microphone, a camera, a sensor), whether gradually (e.g., by whole values, fractional values, 1, 2, 3, 4, 5, 6, 7, 8, 9, 10, tens, 0.1, 0.01, or any multiples of any preceding) within a defined time period (e.g., under about 24, 18, 12, 6, 4, 3, 2, 1 hours) or suddenly, whether based on a user manual input (e.g., via a user input device, a touchscreen, a keyboard, a button, a switch, a dial, a knob, a slider, a cursor device, a microphone, a camera, a sensor) or a set of criteria or thresholds or a regimen.

A sample default setting for the auditory frequency is about 150 Hz and can increase to about 250 Hz, whether gradually (e.g., by whole values, fractional values, 1, 2, 3, 4, 5, 6, 7, 8, 9, 10, tens, 0.1, 0.01, or any multiples of any preceding) within a defined time period (e.g., under about 24, 18, 12, 6, 4, 3, 2, 1 hours) or suddenly, whether based on a user manual input (e.g., via a user input device, a touchscreen, a keyboard, a button, a switch, a dial, a knob, a slider, a cursor device, a microphone, a camera, a sensor) or a set of criteria or thresholds or a regimen.

At start-up phase 54, the control module 12 (e.g., the processor 14) is further configured (e.g., programmed) to request the first and second light sources to flash the first-left-color, within the first light frequency range, to the left visual fields of both eyes and to flash the first-right-color, within the first light frequency range, to the right visual fields of both eyes for the first time duration, whether simultaneously, alternating, or sequentially, whether for each eye or for each visual field.

Steps 56A/B and 58A/B indicate (e.g., visually via the lights or audibly via the sounds) an inspiration and hold of breath phase to the user, where the control module 12 (e.g., the processor 14) is configured (e.g., programmed) to request the first and second light sources to flash the second-left-color, within the second light frequency range, in the left visual fields of both eyes and to flash the second-right-color, within the second light frequency range, in the right visual fields of both eyes for the second time duration, whether simultaneously or sequentially, whether for each eye or for each visual field.

Step 60A/B indicates (e.g., visually via the lights or audibly via the sounds) the start of an expiration of breath phase to the user, where the control module 12 (e.g., the processor 14) is configured (e.g., programmed) to request the first and second light sources to change (e.g., update) from flashing the second-left-color to the third-left-color, within the third light frequency range, in the left visual fields of both eyes and change (e.g., update) the second-right-color to the third-right-color, within the third light frequency range, in the right visual fields of both eyes, whether simultaneously or sequentially, whether for each eye or for each visual field.

Throughout or during the inspiration/hold and expiration phases, as indicated visually via the lights or audibly via the sounds, heart rate and/or heart rate variability of the user is monitored by the HRV module 22 (e.g., a suitable sensor) and the treatment process, as indicated visually via the light or audibly via the sounds, returns to the inspiration and hold breath phases 56A/B and 58A/B until the third time duration expires.

In one example, for the in-breath phase (56A and 56B): the light color may change (e.g., update) from the start-up colors to another color (but a color change is not necessary from start-up). The intensity (or other illumination property) of the entraining lights from the light component 20 can start low and gradually increases in brightness within a pre-set time period or rate of increase to encourage the user 32 to gently breath in.

During a hold phase (steps 58A and 58B), the color (or other illumination property) and any auditory stimulation are not changed (although this is possible) from those established at the inspiration phase (steps 56A and 56B).

During an expiration phase (steps 60A and 60B), the light changes color (or other illumination property) at step 60A from color BL to a color CL (left visual fields of both eyes) and from color BR to a color CR (right visual fields of both eyes), whether simultaneously, alternating, or serially, whether for each eye or for each visual field. The intensity (or other illumination property) of the entraining lights from the light component 20 can gradually fade within a pre-set time period or rate of fade at step 60A in brightness (or other illumination property) to encourage the user 32 to gently breath out.

Any entraining tones from the sound component 18 can become gently quieter, whether gradually within a pre-set time period or rate of change, and the tones also become lower in pitch, whether gradually within a pre-set time period or rate of change, at step 60B, which carries a further relaxing effect. In general, the sound and light intensity (or other illumination or sound properties) is increased, for any given color/tone, during the inspiration phase and decreases during the expiration phase, whether gradually within a pre-set time period or rate of change, whether for each eye or each visual field or each ear.

All breath-in, hold and breath-out effects in color and tone pitch are adjustable by the user 32 via a user input device (e.g., a touchscreen, a keyboard, a button, a switch, a dial, a knob, a slider, a cursor device, a microphone, a camera, a sensor) included in the system 10 and in communication with the module 12 or the unit 24. Entrainment frequency from the sub-delta to the gamma brain wave bands (about 0.1 Hz-about 50 Hz) are also adjustable by the user 32 via a user input device (e.g., a touchscreen, a keyboard, a button, a switch, a dial, a knob, a slider, a cursor device, a microphone, a camera, a sensor) included in the system 10 and in communication with the module 12 or the unit 24.

Figure 4:
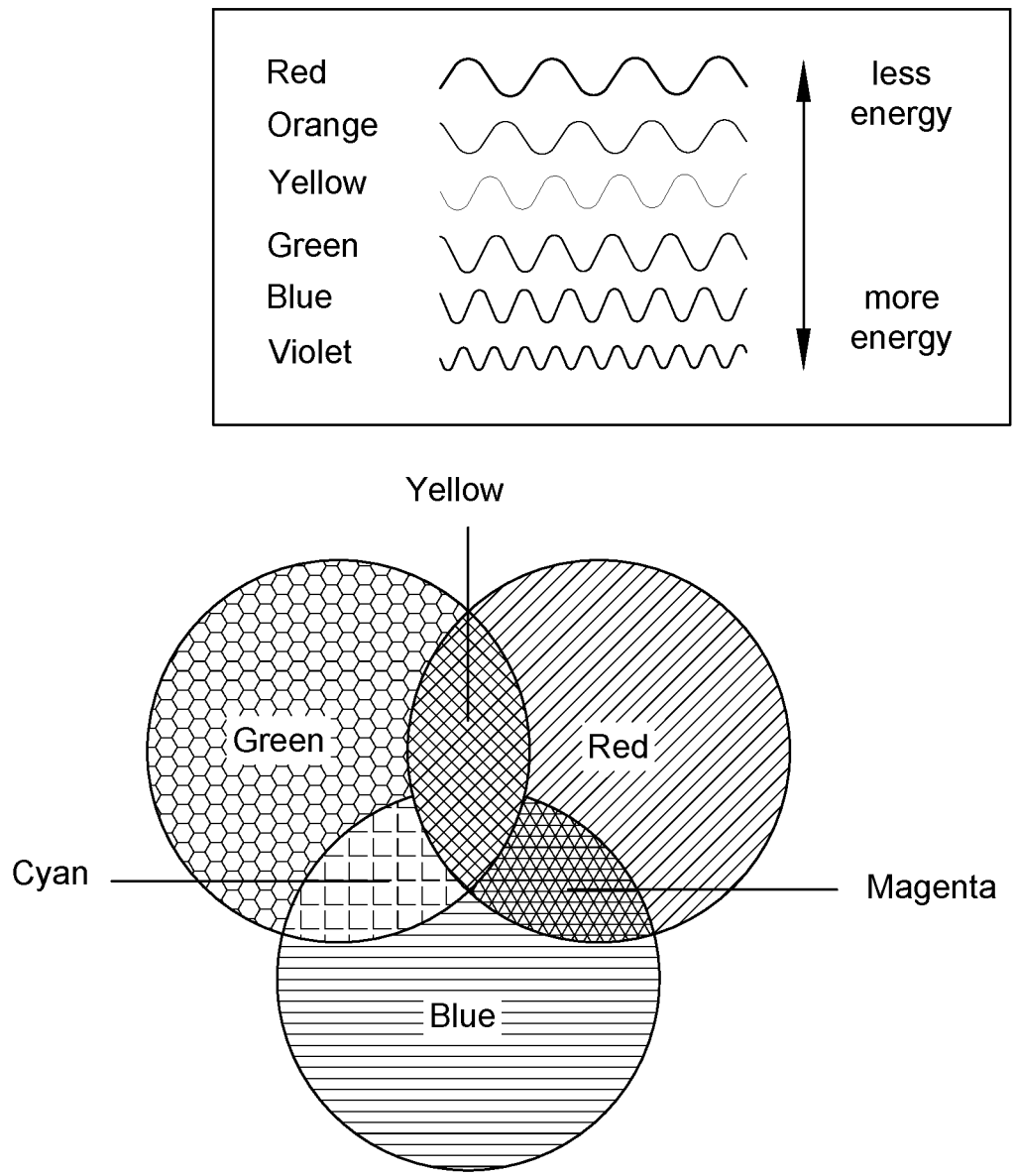
FIG. 4 illustrates an embodiment of a primary colors diagram and a mixing chart according to this disclosure.

To review the primary colors that can be used by the light component 20, consider FIG. 4 that shows an embodiment of a diagram of the three primary colors: red, blue, and green. In terms of mixing these primary colors: red+green=yellow; red+blue=magenta; and green+blue=cyan. The varying energy and frequency of each color is also illustrated: red being low frequency/less energy and violet/magenta being high frequency/more energy.

As described herein, the light component 20 having a LED type lights generates the light stimulation to the eyes of the user 32. The color(s) used during the visual stimulation is user selectable via a user input device (e.g., a touchscreen, a keyboard, a button, a switch, a dial, a knob, a slider, a cursor device, a microphone, a camera, a sensor) included in the system 10 and in communication with the module 12 or the unit 24. The inspiration (in-breath) phase of a breath cycle is sympathetic in that physical arousal and heartbeat frequency increases. Red light stimulates the nervous system (i.e., sympathetic activity). However, red can be quite stimulating, so a blend of red and blue colors (i.e., pink/magenta/violet) can also be used for the in-breath.

The expiration (out-breath) phase of a breath cycle is parasympathetic in that physical arousal and heartbeat frequency decreases. Blue and green colors produce relaxing effects on the nervous system (i.e., parasympathetic), so a blend of blue and green colors (i.e., cyan) can be used for the out-breath. The choice of colors can be selectable and adjustable by the user using HRV module 22 or via a user input device (e.g., a touchscreen, a keyboard, a button, a switch, a dial, a knob, a slider, a cursor device, a microphone, a camera, a sensor) included in the system 10 and in communication with the module 12 or the unit 24.

Example 1

The start-up color indicated below occur in both visual fields of both eyes, whether simultaneously, alternating, or sequentially, whether for each eye or for each visual field. However, this is not required as the left and right visual fields of both eyes can be stimulated with different colors, whether simultaneously, alternating, or sequentially, whether for each eye or for each visual field.

Start-up: color is pink for both eyes (both L/R visual fields) and sound frequency is about 150 Hz, whether simultaneously, alternating, or sequentially, whether for each eye or for each visual field or for each ear; and inspiration (in-breath): color remains pink for both eyes (both L/R visual fields), whether simultaneously, alternating, or sequentially, whether for each eye or for each visual field.

When two colors are used, whether simultaneously, alternating, or sequentially, whether for each eye or for each visual field, the color nearer the red end of the visual spectrum is emitted from the right visual fields (of both eyes), whether simultaneously, alternating, or sequentially, whether for each eye or for each visual field, to cause or produce greater activation to the left brain when compared to the right brain. The audio pitch can increase, whether gradually within a pre-set time period or rate of change, to a user selectable level via a user input device (e.g., a touchscreen, a keyboard, a button, a switch, a dial, a knob, a slider, a cursor device, a microphone, a camera, a sensor) included in the system 10 and in communication with the module 12 or the unit 24, but is typically about 250 Hz. The volume also increases, whether gradually within a pre-set time or rate of change.

Hold phase: no changes to color, brightness and intensity, whether simultaneously, alternating, or sequentially, whether for each eye or for each visual field, or to sound frequency or volume, whether simultaneously, alternating, or sequentially; and expiration phase (out-breath): color change (e.g., update) to blue in left visual fields of both eyes and green in the right visual fields of both eyes (green is nearer the red end of the spectrum than blue is), whether simultaneously, alternating, or sequentially, whether for each eye or for each visual field, whether gradually within a pre-set time period or rate of change. The audio stimulation shifts down in pitch (from about 250 Hz to about 150 Hz) and volume is reduced, each whether gradually within a pre-set time period or rate of change; and return to inspiration phase and cycle repeats (i.e., inspiration-hold-expiration).

Example 2

Take Example 1 and modify the inspiration/expiration colors as follows:

Two colors are used for inspiration: a first color for the left visual fields of both eyes and a second different color for the right visual fields of both eyes, whether simultaneously, alternating, or sequentially, whether for each eye or for each visual field. Both colors are nearer the red end of the spectrum compared with the exhalation colors and the color in the right visual fields would be most near the red end of the spectrum (for greater left-brain activation). The inhalation colors, in this Example 2, are teal/cyan on the left visual fields and yellow in the right visual fields. If yellow is used in the left visual fields, then orange or red would be used in the right visual fields of both eyes.

This combination of blue and green (teal/cyan) is mildly sympathetic. On occasion, when the users' arousal is very low, such as with adrenal insufficiency or adrenal fatigue, red or a blend of yellow in the left visual fields and red in the right visual fields may be used.

Further, for any of the inspiration or expiration phases above, color stimulation can be blue in the left visual fields of both eyes and yellow in the right visual fields of both eyes or green in the left visual fields of both eyes and yellow in the right visual fields of both eyes, each whether simultaneously, alternating, or sequentially, whether for each eye or for each visual field.

Other color variations can be used depending on the situation:

(i) a user with PTSD and concussion who can no longer breathe in a relaxed way. This is in part due to the PTSD and in part due to the concussion. The inability to breath in a relaxed way adds to his already high anxiety via a neurological process referred to as afference. Because this person's arousal is so highly activated, inspiration colors of green in the left visual fields and a lighter green in the right visual fields might be used while only blue used during the expiration phase of his breathing cycle, each whether simultaneously, alternating, or sequentially, whether for each eye or for each visual field; and (ii) a person with Lyme disease and, in the process, develops adrenal fatigue can benefit from entrainment assisted HRV breathing. Because this person's arousal is so low, inspiration colors of yellow or orange in the left visual fields and red in the right visual fields might be used. The expiration phase could utilize green in the left visual fields and yellow in the right visual fields, each whether simultaneously, alternating, or sequentially, whether for each eye or for each visual field.

Figure 5:
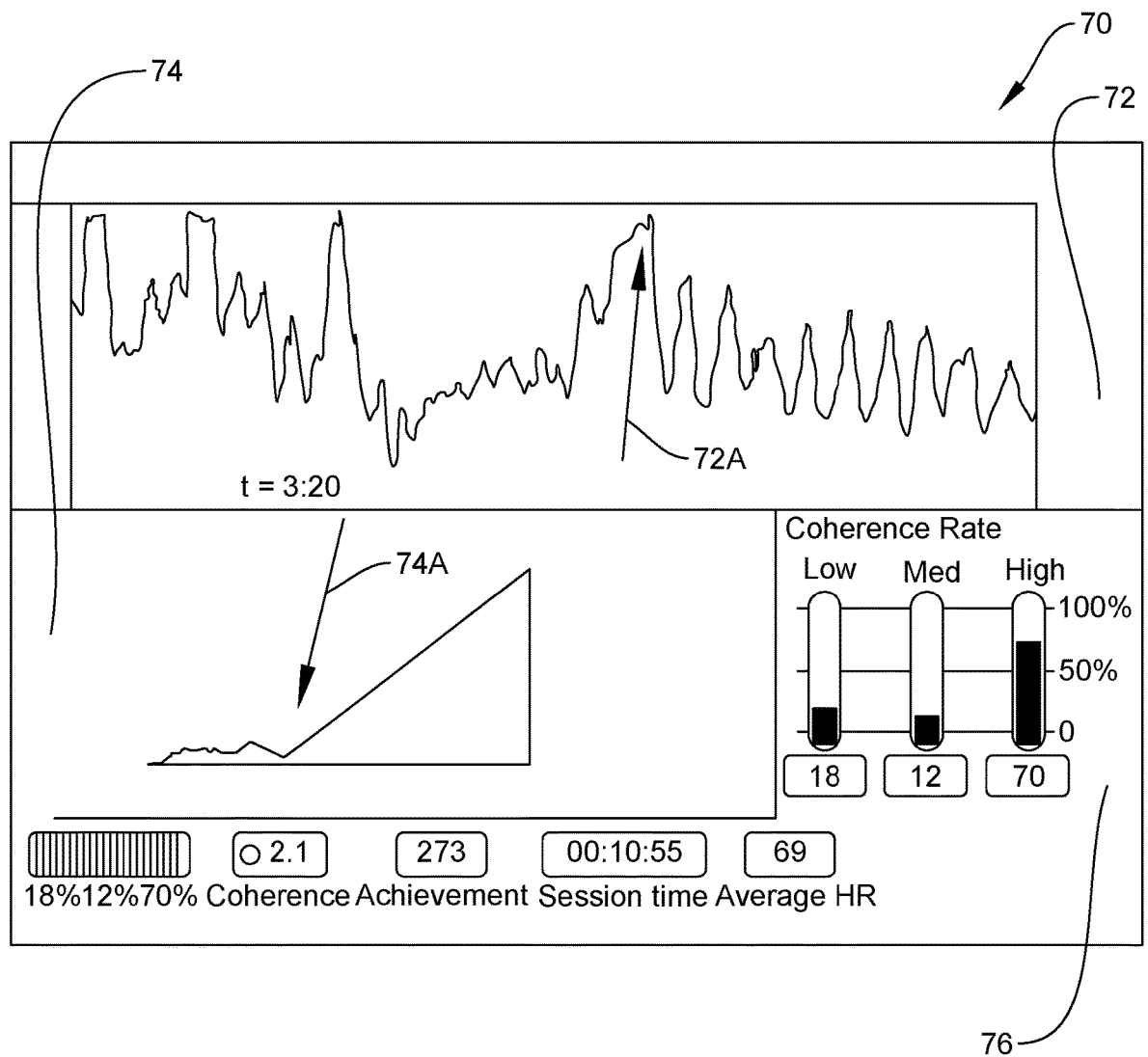
FIG. 5 illustrates an embodiment of a set of sample results from a user that used the method of FIG. 3 according to this disclosure.

FIG. 5 shows an embodiment of a representation 70 of heart rate variability (HRV) using an infrared heart pulse monitor and EM-Wave Pro software (by Heart Math Inc.) according to this disclosure. Good or sufficient HRV control is characterized by smooth sine wave shaped waveforms and a 10-15 beat/minute swing in heartbeat between inspiration and expiration. A main upper panel 72 shows heart rate in beats per minute in real time. Shortly after the user applied the method 50 (at 3:20, see arrow 72A), as disclosed herein, the graph illustrates that the HRV improved considerably. A lower left panel 74 illustrates other characteristics of HRV, such as swing between inspiration and expiration phases and the smooth (sine wave) shaped waveform (see arrow 74A). A lower right panel 76 shows the coherence rate: a ratio of "good" HRV vs "bad" HRV as an average of the entire session.

Figure 6:
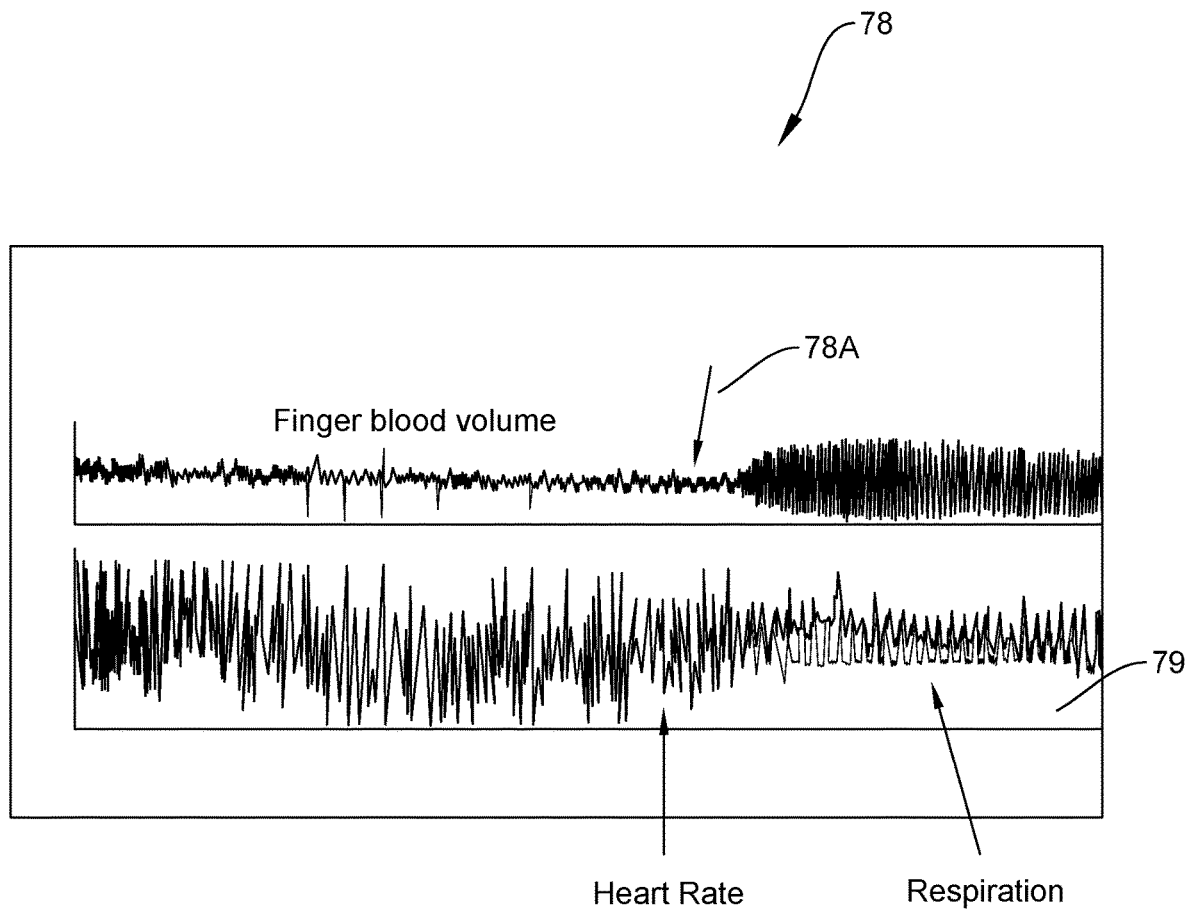
FIG. 6 illustrates an embodiment of a set of sample results with hypertension monitoring from a user that used the method of FIG. 3 according to this disclosure.

FIG. 6 illustrates various embodiments of representations of tracing graphs 78 that indicate that during states of heightened arousal, as experienced during stress (e.g., anxiety, PTSD, sympathetic activity), it is common to have vasoconstriction in the periphery of the body, such as fingers and toes.

The analysis of finger blood volume using a plethysmograph, breathing using a chest band with an isometric transducer and heart rate variability (HRV) using an infrared heart pulse monitor and Cardio Pro (HRV software manufactured by Thought Technologies Inc.). This person was considered "untrainable" using standard HRV technologies. Prior to using the method 50 (before arrow 78A), as disclosed herein, that the heart rate was desynchronized from the user's breathing and finger blood volume was very shut down (and hence cold fingers). Shortly after this person applied the method 50 (at 9:00 see arrow 88A), as disclosed herein, that the finger blood volume and HRV improved considerably. The illustration shows how the heart rate began "nesting" into her respiration (lower graph 79 of FIG. 6).

Example 3

Figure 7:
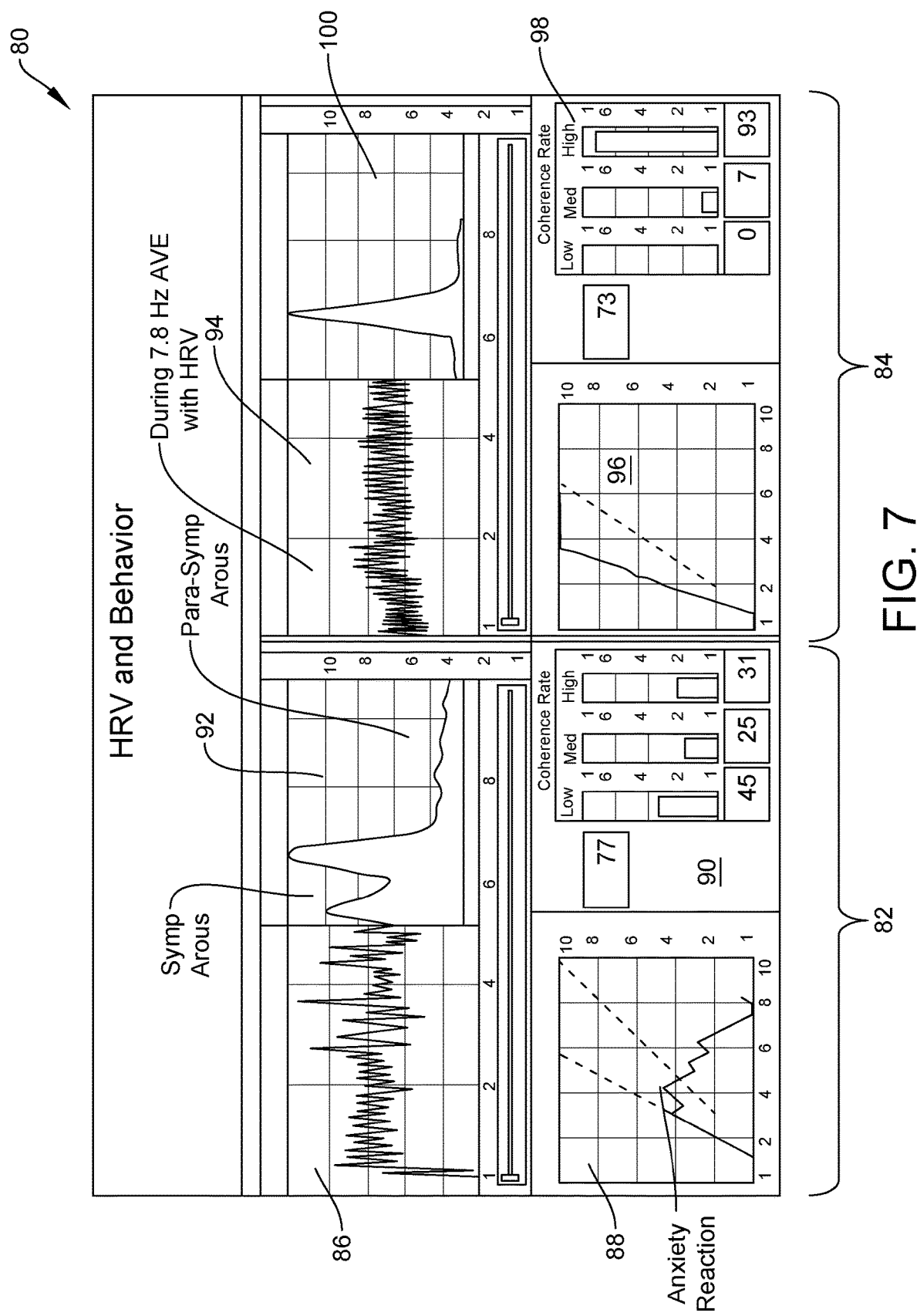
FIG. 7 illustrates an embodiment of a representation HR and HRV characteristics before and after using the method of FIG. 3 according to this disclosure.

FIG. 7 illustrates an embodiment of a representation of a screen 80 from "EmWavePC" by Heart Math showing poor heart rate variability (HRV) of a user with anxiety before and after using the AVE/HRV method 50, as disclosed herein. The screen 80 illustrates a pre-AVE/HRV block 82 and a treatment AVE/HRV block 84. The pre-AVE/HRV block 82 includes four panels (or windows or panes) 86, 88, 90 and 92. The panel 86 illustrates the user's actual heart rate while breathing in and out and shows heart rate beginning to degrade at around three minutes when anxiety builds during monitoring. The panel 88 illustrates a graph of the user's performance, which deteriorated after three minutes and indicated high distress at the end of the monitoring period.

The panel 90 in the block 82 shows an average heart rate of 77 and a poor breathing/HRV ratio. This finding means that instead of responding to baro-receptor feedback off the aorta, the heart is mainly responding to negative thoughts. The panel 92 in the block 82 is a spectral display of HRV while using the paced breathing method 50 as disclosed herein: in this example the user breathe in for 5-seconds and out for 5-seconds thereby representing a 10-second breathing cycle. The user's spectra are exhibited at about 0.1 Hz. The lower frequencies represent trending and sympathetic activity. Frequencies above about 0.1 Hz represent parasympathetic activity as the nervous system tries to counteract sympathetic arousal. Given that the autonomic nervous system consists of both the sympathetic and parasympathetic systems, the data shows an over-active autonomic nervous system associated with anxiety.

Consider panels 94, 96, 98 and 100 in the AVE/HRV block 84 that provide data illustrations during use of the AVE/HRV method 50 showing the user beginning to dissociate from anxious thoughts that in turn stabilizes her HRV together with the drop in anxiety. The raw data of panel 94 shows a very stable pattern in comparison to her pre-AVE/HRV (see panel 86). Panel 96 shows an effectively perfect result for the user regarding anxiety stabilization. The panel 98 shows a lower heart rate of 73 and a relatively excellent or adequate heart response to breathing. The panel 100 (spectral graph) shows a relatively excellent or adequate heart response to breathing as illustrated by the absence of both low and high frequency components (representing low anxiety and low autonomic nervous system activity). The user is relaxed.

Because AVE is so powerful at relaxing people, it may be often used as triage in emergency conditions where a person is undergoing a panic attack in relation to a traumatic event, PTSD, etc. In some cases, a person needs to be "tuned" to a more optimal breath. In this case the height or "power" of the breath-entrained heart rate at the frequency of breathing (e.g., a 10-second breath-cycle is about 0.1 Hz while an 8-second breath cycle is about 0.125 Hz). Because breathing too fast or too slow can also trigger anxiety or reduce the relaxation response to AVE, which shows up as low (sympathetic) and high (parasympathetic) frequency components, sometimes it helps to tune the breathing to be optimal for that person. The user can then use the method 50 as disclosed herein to achieve the desired outcome.

Figure 8:
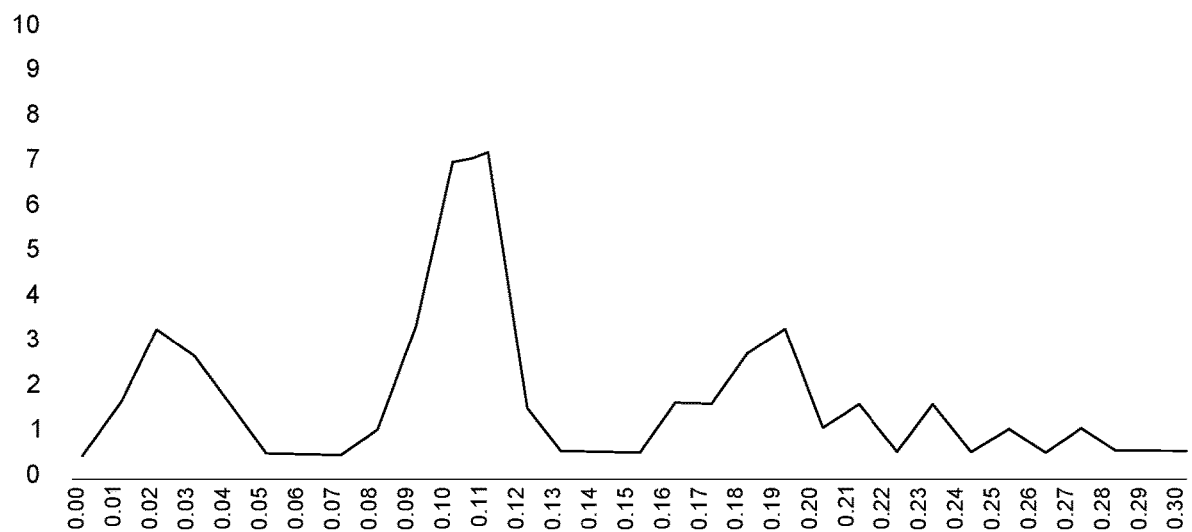
FIG. 8 illustrates an embodiment of a graph of HRV v. frequency spectra representative of a poor response according to this disclosure.
Figure 9:
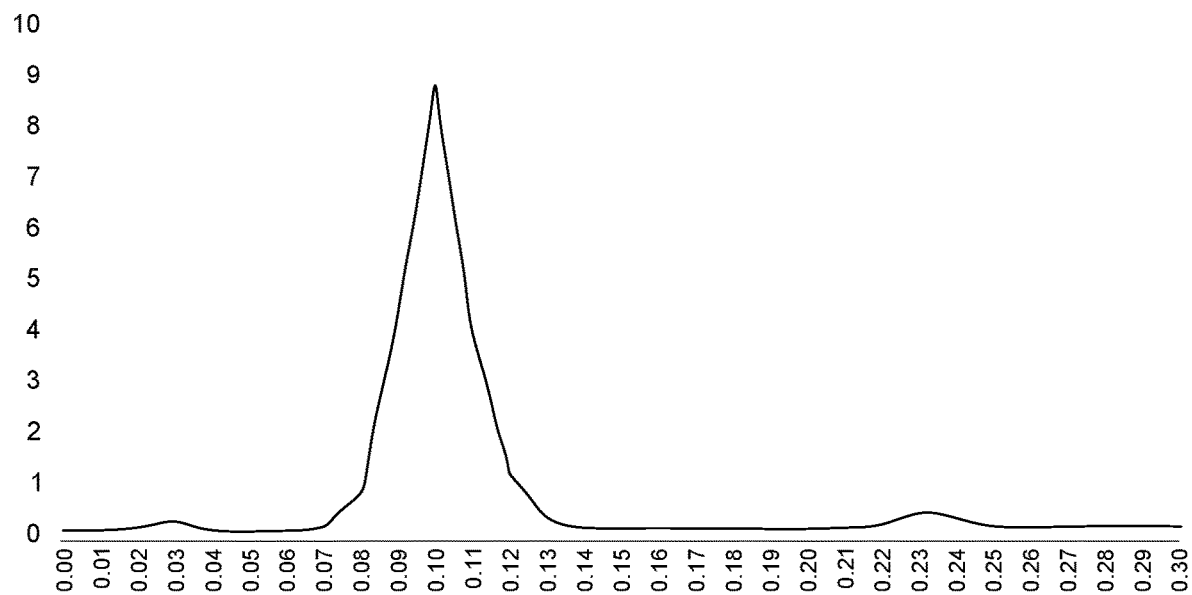
FIG. 9 illustrates an embodiment of a graph of HRV v. frequency spectra representative of a good response according to this disclosure.

The graphs of FIGS. 8 and 9 show sub-optimal (FIG. 8), breathing too slow or too fast, versus breathing just right (FIG. 9).

In summary, the method 50, as disclosed herein, can provide at least one of the following:

deep relaxation for the user through the presentation of audio and visual stimulation to the user at various brain wave frequencies;

visual inspiration and expiration breathing cues to the user through color changes in the eye set worn by the user;

visual inspiration and expiration breathing cues to the user through audio tonal changes delivered through the headphones (or speakers) worn by the user;

an increasing and decreasing the intensity of the pulsed lights and pulsed tones to the user in order to elicit or cause a natural response in the user to breathe in and out;

deliver either visual or tonal breathing cues to the user simultaneously with entrainment in the brain wave range of about 0.1 Hz to about 50 Hz; or enable or cause the user to measurably feel or measurably experience that the inspirational cues, either color and/or tonal changes presented to the user, measurably feels more like a suggestion and less of a demand, and therefore enable or cause the user not to get anxious from the worry of failing, but relaxes and easily learns to follow the cues presented to the user while also simultaneously becoming deeply relaxed from the AVE therapy.

Example embodiments include:

A method for stimulating a central nervous system of a human subject and a plurality of brain waves of the human subject, each for an application period, the human subject having a left eye and a right eye and a left ear and a right ear, by audio-visual entrainment (AVE) to provide a plurality of breathing cues for training heart rate variability in the human subject administered by an AVE apparatus having a light source for providing a left visual field flashing light signal to both eyes of the human subject and a right visual field flashing light signal to both eyes of the human subject and a sound source, operable independently of the light source, for providing a left side pulsating sound signal to the left ear of the human subject and a right side pulsating sound signal to the right ear of the human subject and a controller operably connected to the light source and the sound source for changing color and brightness or intensity of the flashing light signals and for changing pitch, loudness or tone of the pulsating sound signals, the method comprising:

for a start-up phase, administering (i) the left side flashing light signal having a color AL to the left visual field of both eyes of the human subject and (ii) the right side flashing light signal having a color AR to the right visual field of both eyes of the human subject;

for an inspiration phase, administering (i) the left side flashing light signal having a color BL and (ii) the right side flashing light signals having a color BR to provide an in-breath cue to the human subject;

for a hold breath phase, maintaining colors BL and BR and intensity as per step (b);

for an expiration phase, changing (i) the left side flashing light signal from the color BL to a color CL and (ii) the right side flashing light signal from the color BR a color CR to provide an out-breath cue to the human subject; and optionally repeating steps at least one of (b), (c) or (d) for the application period.

The method as above, wherein the colors AL and AR are the same; the colors BL and BR are the same; the colors CL and CR are the same; and the colors BL and BR are different from the colors CL and CR, respectively.

The method as above, wherein at least one color BL and BR is the same as the color AL.

The method as above, wherein the colors AL and AR are pink; the colors BL and BR are pink; the color CL is blue; and the color CR is green.

The method as above, wherein the colors BL and BR are different; and the colors CL and CR are different; the colors BL and BR are different from the colors CL and CR, respectively.

The method as above, wherein during the inspiration phase step (b) the method further comprising increasing the brightness of the left and right flashing light signals.

The method as above, wherein during the expiration phase step (d) the method further comprising decreasing the brightness of the left and right flashing light signals.

The method as above, further comprising administering the left side pulsating sound signal to the left ear and the right side pulsating sound signal to the right ear of the subject; and changing the pitch, loudness or tone of the pulsating sound signals from a first frequency or amplitude to a second frequency or amplitude to provide auditory inspiration and expiration breathing cues to the subject that are coordinated with steps (b) and (d).

The method as above, wherein during the in-breath phase the pitch, loudness or tone of the pulsating sound signals is increased.

The method as above, wherein during the out-breath phase the pitch, loudness or tone of the pulsating sound signals is reduced.

What is claimed is:

1. A method comprising:

causing a headwear unit to be worn by a user having a right eye and a left eye, wherein the right eye has a first right visual field and a first left visual field, wherein the left eye has a second right visual field and a second left visual field, wherein the headwear unit hosts a processor, a first light source configured for stimulating the first right visual field of the right eye and the first left visual field of the right eye when requested by the processor while the headwear unit is worn by the user, and a second light source configured for stimulating the second right visual field of the left eye and the second left visual field of the left eye when requested by the processor while the headwear unit is worn by the user;

causing the processor to read a first set of parameters, a second set of parameters, and a third set of parameters, wherein the first set of parameters includes a first-left-color (AL) identifier, a first-right-color (AR) identifier, a first light frequency range, and a first time duration, wherein the second set of parameters includes a second-left-color (BL) identifier, a second-right-color (BR) identifier, a second light frequency range, and a second time duration, and wherein the third set of parameters includes a third-left-color (CL) identifier, a third-right-color (CR) identifier, a third light frequency range, and a third time duration;

causing the processor to request the first light source and the second light source (a) to flash a first-left-color, within the first light frequency range, to the first left visual field and the second left visual field for the first time duration based on the first-left-color (AL) identifier and (b) to flash a first-right-color, within the first light frequency range, to the first right visual field and the second right visual field for the first time duration based on the first-right-color (AR) identifier;

causing the processor to request the first light source and the second light source (a) to flash a second-left-color, within the second light frequency range, in the first left visual field and the second left visual field for the second time duration based on the second-left-color (BL) identifier and (b) to flash a second-right-color, within the second light frequency range, in the first right visual field and the second right visual field for the second time duration based on the second-right-color (BR) identifier such that the user is visually instructed to start an inspiration and hold of breath phase;

causing the processor to request the first light source and the second light source (a) to change from flashing the second-left-color to a third-left-color, within the third light frequency range, in the first left visual field and the second left visual field based on the third-left-color (CL) identifier and (b) to change the second-right-color to a third-right-color, within the third light frequency range, in the first right visual field and the second right visual field based on the third-right-color (CR) identifier such that the user is visually instructed to start an expiration of breath phase to the user after the inspiration and hold of breath phase; and causing the processor to request a heart rate monitor to monitor at least one of a heart rate of the user or a heart rate variability of the user throughout at least one of the inspiration and hold breath phase or the expiration of breath phase until the third time duration expires.

2. The method of claim 1, further comprising:
causing a speaker to be worn by the user such that the processor requests the speaker to generate a set of sound pulses to the user within a pitch range, a tone range, and a volume range, wherein the set of sound pulses varies within at least one of the pitch range, the tone range, or the volume range when the inspiration and hold breath phase begins and when the expiration breath phase begins.

3. The method of claim 1, wherein the first-left-color (AL) and the first-right-color (AR) are the same; the second-left-color (BL) and the second-right-color (BR) are the same; the third-left-color (CL) and the third-right-color (CR) are the same; and the colors BL and BR are different from the colors CL and CR, respectively.

4. The method of claim 3, wherein at least one of the second-left-color (BL) and the second-right-color (BR) is the same as the first-left-color (AL).

5. The method of claim 3, wherein the first-left-color (AL) and the first-right-color (AR) are pink; the second-left-color (BL) and the second-right-color (BR) are pink; the third-left-color (CL) is blue; and the third-right-color (CR) is green.

6. The method of claim 1, wherein the second-left-color (BL) and the second-right-color (BR) are different; and the third-left-color (CL) and the third-right-color (CR) are different; the second-left-color (BL) and the second-right-color (BR) are different from the third-left-color (CL) and the third-right-color (CR), respectively.

7. The method of claim 1, further comprising:
causing the processor to request the first light source and the second light source to increase a brightness of the second-left-color (BL) and second-right-color (BR) when the inspiration and hold breath phase begins.

8. The method of claim 7, further comprising:
causing the processor to request the first light source and the second light source to decrease the brightness of the third-left-color (CL) and third-right-color (CR) when the expiration and breath phase begins.

9. The method of claim 1, further comprising:
causing the processor to request the heart rate monitor to monitor at least one of the heart rate of the user or the heart rate variability of the user throughout the inspiration and hold breath phase and the expiration of breath phase until the third time duration expires.

10. The method of claim 1, further comprising:
causing the processor to request the heart rate monitor to monitor the heart rate of the user throughout at least one of the inspiration and hold breath phase or the expiration of breath phase until the third time duration expires.

11. The method of claim 1, further comprising:
causing the processor to request the heart rate monitor to monitor the heart rate variability of the user throughout at least one of the inspiration and hold breath phase or the expiration of breath phase until the third time duration expires.

12. The method of claim 1, wherein the headwear unit includes a frame hosts the first light source and the second light source.

13. The method of claim 1, wherein the headwear unit includes an arm hosting a speaker that generates a set of sound pulses to the user within a pitch range, a tone range, and a volume range, wherein the set of sound pulses varies within at least one of the pitch range, the tone range, or the volume range when the inspiration and hold breath phase begins and when the expiration breath phase begins.

14. The method of claim 1, further comprising:
causing the processor to request the first light source and the second light source (a) to gradually change from flashing the second-left-color to a third-left-color, within the third light frequency range, in the first left visual field and the second left visual field based on the third-left-color (CL) identifier and (b) to gradually change the second-right-color to a third-right-color, within the third light frequency range, in the first right visual field and the second right visual field based on the third-right-color (CR) identifier such that the user is visually instructed to start the expiration of breath phase to the user after the inspiration and hold of breath phase.

15. The method of claim 1, further comprising:
causing the processor to request the first light source and the second light source (a) to suddenly change from flashing the second-left-color to a third-left-color, within the third light frequency range, in the first left visual field and the second left visual field based on the third-left-color (CL) identifier and (b) to suddenly change the second-right-color to a third-right-color, within the third light frequency range, in the first right visual field and the second right visual field based on the third-right-color (CR) identifier such that the user is visually instructed to start the expiration of breath phase to the user after the inspiration and hold of breath phase.

16. The method of claim 1, wherein the headwear unit includes the heart rate monitor.

17. The method of claim 1, wherein the headwear unit does not include the heart rate monitor.

18. The method of claim 1, wherein each of the second-left-color (BL) and the second-right-color (BR) is not a primary color.

19. A memory storing a set of instructions executable by a processor of a headwear unit when the headwear unit is worn by a user having a right eye and a left eye, wherein the right eye has a first right visual field and a first left visual field, wherein the left eye has a second right visual field and a second left visual field, wherein the headwear unit hosts a processor, a first light source configured for stimulating the first right visual field of the right eye and the first left visual field of the right eye when requested by the processor while the headwear unit is worn by the user, and a second light source configured for stimulating the second right visual field of the left eye and the second left visual field of the left eye when requested by the processor while the headwear unit is worn by the user, wherein the set of instructions causes the processor to:
read a first set of parameters, a second set of parameters, and a third set of parameters, wherein the first set of parameters includes a first-left-color (AL) identifier, a first-right-color (AR) identifier, a first light frequency range, and a first time duration, wherein the second set of parameters includes a second-left-color (BL) identifier, a second-right-color (BR) identifier, a second light frequency range, and a second time duration, and wherein the third set of parameters includes a third-left-color (CL) identifier, a third-right-color (CR) identifier, a third light frequency range, and a third time duration;
request the first light source and the second light source (a) to flash a first-left-color, within the first light frequency range, to the first left visual field and the second left visual field for the first time duration based on the first-left-color (AL) identifier and (b) to flash a first-right-color, within the first light frequency range, to the first right visual field and the second right visual field for the first time duration based on the first-right-color (AR) identifier;
request the first light source and the second light source (a) to flash a second-left-color, within the second light frequency range, in the first left visual field and the second left visual field for the second time duration based on the second-left-color (BL) identifier and (b) to flash a second-right-color, within the second light frequency range, in the first right visual field and the second right visual field for the second time duration based on the second-right-color (BR) identifier such that the user is visually instructed to start an inspiration and hold of breath phase;
request the first light source and the second light source (a) to change from flashing the second-left-color to a third-left-color, within the third light frequency range, in the first left visual field and the second left visual field based on the third-left-color (CL) identifier and (b) to change the second-right-color to a third-right-color, within the third light frequency range, in the first right visual field and the second right visual field based on the third-right-color (CR) identifier such that the user is visually instructed to start an expiration of breath phase to the user after the inspiration and hold of breath phase; and
request a heart rate monitor to monitor at least one of a heart rate of the user or a heart rate variability of the user throughout at least one of the inspiration and hold breath phase or the expiration of breath phase until the third time duration expires.

20. A device including:
a headwear unit configured to be worn by a user having a right eye and a left eye, wherein the right eye has a first right visual field and a first left visual field, wherein the left eye has a second right visual field and a second left visual field, wherein the headwear unit hosts a processor, a first light source configured for stimulating the first right visual field of the right eye and the first left visual field of the right eye when requested by the processor while the headwear unit is worn by the user, and a second light source configured for stimulating the second right visual field of the left eye and the second left visual field of the left eye when requested by the processor while the headwear unit is worn by the user, wherein the processor is programmed to:
read a first set of parameters, a second set of parameters, and a third set of parameters, wherein the first set of parameters includes a first-left-color (AL) identifier, a first-right-color (AR) identifier, a first light frequency range, and a first time duration, wherein the second set of parameters includes a second-left-color (BL) identifier, a second-right-color (BR) identifier, a second light frequency range, and a second time duration, and wherein the third set of parameters includes a third-left-color (CL) identifier, a third-right-color (CR) identifier, a third light frequency range, and a third time duration;
request the first light source and the second light source (a) to flash a first-left-color, within the first light frequency range, to the first left visual field and the second left visual field for the first time duration based on the first-left-color (AL) identifier and (b) to flash a first-right-color, within the first light frequency range, to the first right visual field and the second right visual field for the first time duration based on the first-right-color (AR) identifier;
request the first light source and the second light source (a) to flash a second-left-color, within the second light frequency range, in the first left visual field and the second left visual field for the second time duration based on the second-left-color (BL) identifier and (b) to flash a second-right-color, within the second light frequency range, in the first right visual field and the second right visual field for the second time duration based on the second-right-color (BR)

identifier such that the user is visually instructed to start an inspiration and hold of breath phase;

request the first light source and the second light source (a) to change from flashing the second-left-color to a third-left-color, within the third light frequency range, in the first left visual field and the second left visual field based on the third-left-color (CL) identifier and (b) to change the second-right-color to a third-right-color, within the third light frequency range, in the first right visual field and the second right visual field based on the third-right-color (CR) identifier such that the user is visually instructed to start an expiration of breath phase to the user after the inspiration and hold of breath phase; and request a heart rate monitor to monitor at least one of a heart rate of the user or a heart rate variability of the user throughout at least one of the inspiration and hold breath phase or the expiration of breath phase until the third time duration expires.

\* \* \* \* \*